(12) United States Patent
Williams et al.

(10) Patent No.: US 11,844,509 B2
(45) Date of Patent: *Dec. 19, 2023

(54) FIXATION DEVICE

(71) Applicant: WEST GEN TECHNOLOGIES, L.L.C., Plainview, TX (US)

(72) Inventors: Donald A. Williams, Plainview, TX (US); George J. Sikora, Bridgewater, MA (US)

(73) Assignee: West Gen Technologies, L.L.C., Plainview, TX (US)

( * ) Notice: Subject to any disclaimer, the term of this patent is extended or adjusted under 35 U.S.C. 154(b) by 275 days.

This patent is subject to a terminal disclaimer.

(21) Appl. No.: 16/846,711

(22) Filed: Apr. 13, 2020

(65) Prior Publication Data

US 2020/0237363 A1 Jul. 30, 2020

Related U.S. Application Data

(63) Continuation of application No. 16/429,310, filed on Jun. 3, 2019, now Pat. No. 10,624,626.

(Continued)

(51) Int. Cl.
*A61B 17/04* (2006.01)
*A61B 17/17* (2006.01)
(Continued)

(52) U.S. Cl.
CPC ...... *A61B 17/0401* (2013.01); *A61B 17/0482* (2013.01); *A61B 17/17* (2013.01);
(Continued)

(58) Field of Classification Search
CPC ........ A61B 17/0401; A61B 2017/0412; A61B 2017/0427; A61B 2017/0446;
(Continued)

(56) References Cited

U.S. PATENT DOCUMENTS

| 5,380,334 A | 1/1995 | Torrie et al. |
| 5,387,213 A | 2/1995 | Breard et al. |

(Continued)

OTHER PUBLICATIONS

International Searching Authority, International Search Report and Written Opinion for corresponding application (PCT/US2019/035148), dated Sep. 20, 2019; 11 pages.

*Primary Examiner* — Alexander J Orkin
(74) *Attorney, Agent, or Firm* — Dickinson Wright PLLC; Mark E. Scott

(57) ABSTRACT

A fixation device. At least one example embodiment is a bone anchor comprising: a proximal head; a bollard coupled to the proximal head; a first barb coupled to the bollard, the first barb extends outward a first distance measured perpendicularly from an anchor central axis, the first distance greater than half the transverse dimension of the bollard, and the first barb extends outward at a first radial from the anchor central axis; and a second barb coupled to the first barb, the second barb extends outward a second distance measured perpendicularly from the anchor central axis, the second distance greater than half the transverse dimension of the bollard, and the second barb extends outward at a second radial from the anchor central axis, the second radial at a second rotational orientation at least 36 angular degrees from the first radial.

20 Claims, 6 Drawing Sheets

Related U.S. Application Data

(60) Provisional application No. 62/680,227, filed on Jun. 4, 2018.

(51) Int. Cl.
    *A61F 2/08*     (2006.01)
    *A61B 17/88*     (2006.01)
    *A61B 17/00*     (2006.01)

(52) U.S. Cl.
    CPC ...... *A61B 17/1714* (2013.01); *A61B 17/1796* (2013.01); *A61B 17/8875* (2013.01); *A61B 17/8883* (2013.01); *A61F 2/0805* (2013.01); *A61F 2/0811* (2013.01); *A61B 2017/00986* (2013.01); *A61B 2017/00991* (2013.01); *A61B 2017/0409* (2013.01); *A61B 2017/0412* (2013.01); *A61B 2017/0427* (2013.01); *A61B 2017/0446* (2013.01); *A61B 2017/0464* (2013.01); *A61F 2002/0852* (2013.01); *A61F 2002/0888* (2013.01); *A61F 2002/0894* (2013.01)

(58) Field of Classification Search
    CPC ..... A61B 2017/0403; A61B 2017/0647; A61F 2002/0888; A61F 2002/0858
    See application file for complete search history.

(56) References Cited

U.S. PATENT DOCUMENTS

| | | |
|---|---|---|
| 5,522,843 A | 6/1996 | Zang |
| 5,725,581 A | 3/1998 | Branemark |
| 5,904,704 A | 5/1999 | Goble et al. |
| 6,139,565 A | 10/2000 | Stone et al. |
| 6,267,766 B1 | 7/2001 | Burkhart |
| 6,302,885 B1 | 10/2001 | Essiger |
| 7,699,881 B2 | 4/2010 | Willmann |
| 8,075,588 B2 * | 12/2011 | Berberich .......... A61B 17/0401 606/232 |
| 10,624,626 B2 * | 4/2020 | Williams .............. A61F 2/0811 |
| 2002/0161401 A1 | 10/2002 | Steiner |
| 2003/0088251 A1 | 5/2003 | Braun et al. |
| 2004/0098045 A1 | 5/2004 | Grafton et al. |
| 2004/0153074 A1 | 8/2004 | Bojarski et al. |
| 2005/0107828 A1 | 5/2005 | Reese |
| 2005/0267478 A1 | 12/2005 | Corradi et al. |
| 2007/0198017 A1 | 8/2007 | Tschakaloff et al. |
| 2007/0198018 A1 | 8/2007 | Biedermann et al. |
| 2008/0009904 A1 | 1/2008 | Bourque et al. |
| 2008/0167660 A1 | 7/2008 | Moreau et al. |
| 2009/0125071 A1 | 5/2009 | Skinlo et al. |
| 2010/0004683 A1 | 1/2010 | Hoof et al. |
| 2010/0063541 A1 | 3/2010 | Brunelle et al. |
| 2016/0278760 A1 | 9/2016 | McDevitt |

* cited by examiner

FIXATION DEVICE

CROSS-REFERENCE TO RELATED APPLICATIONS

Ths application is a continuation of U.S. application Ser. No. 16/429,310 fled Jun. 3, 2019 (now U.S. Pat. No. 10,624,626). This application also claims the benefit of U.S. Provisional Application No. 62/680,227 titled "Bone Anchor and Suture System, Tool for Implanting Same, and Method of Implanting Same." Both applications are incorporated by reference herein as if reproduced in full below.

BACKGROUND

Fixation devices, such as a bone anchors, and sutures are used in the related art for attaching soft tissue to bone. The related-art bone anchors may have either a spiral screw thread so that the bone anchors may be screwed into a hole within the bone, or the related-art bone anchors may have a series of conical members stacked and aligned along the main axis of the bone anchor and which engage with the bone material once inserted into a hole in the bone. Related-art bone anchors suffer from several drawbacks. For example, bone anchors with screw threads are relatively difficult to implant since the bone anchors must be screwed into a hole formed in bone. Bone anchors with a series annular grooves may be pressed into a hole formed in bone, but the bone anchors do not always fully engage with bone material and can become dislodged.

BRIEF DESCRIPTION OF THE DRAWINGS

For a detailed description of example embodiments, reference will now be made to the accompanying drawings (not necessarily to scale) in which.

DEFINITIONS

Figure 1:
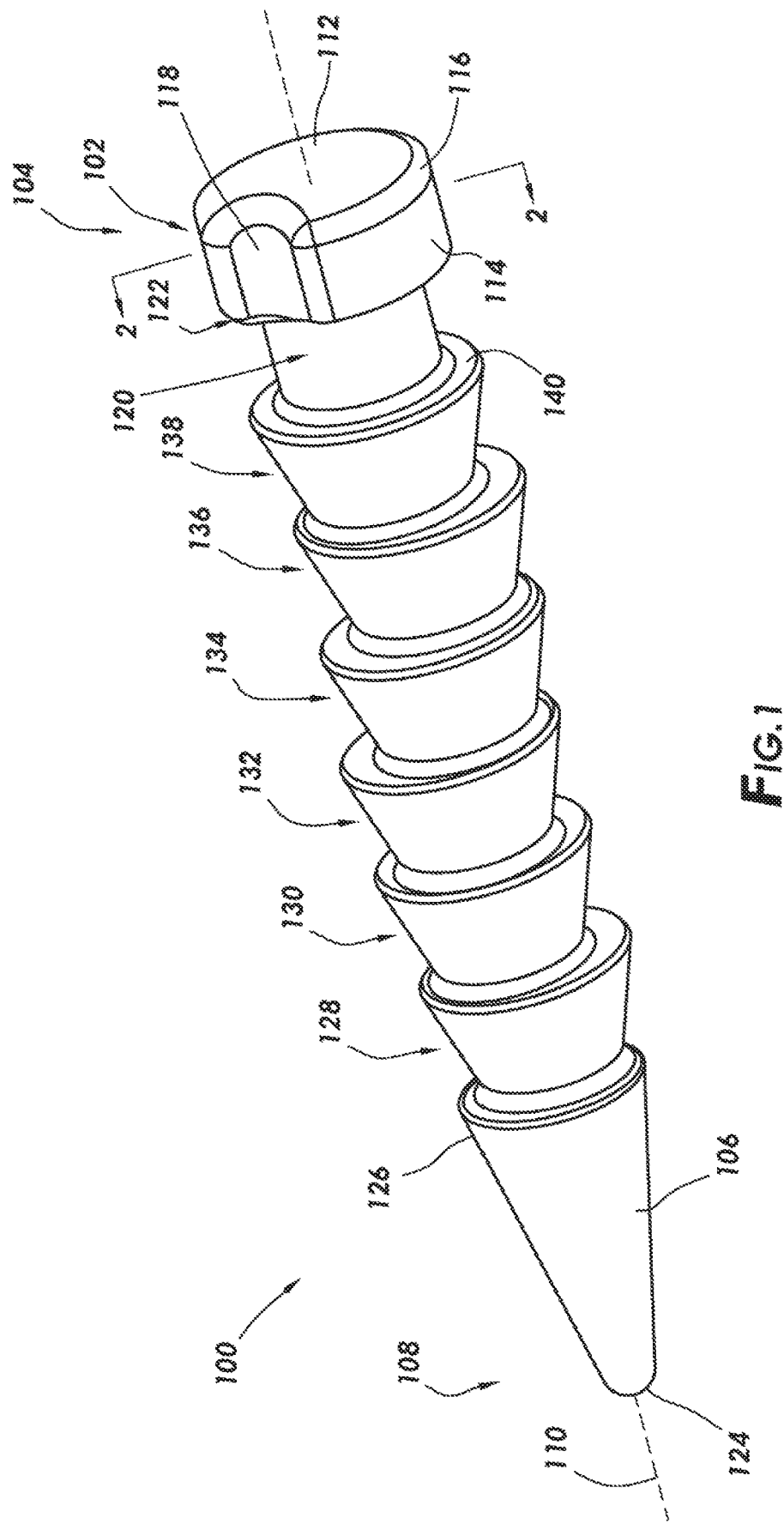
FIG. 1 shows a perspective view of a bone anchor in accordance with at least some embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

"About" in relation to a dimension will be the recited dimension plus or minus ten percent (10%).

"Anchor central axis" shall mean a longitudinal axis of a bone anchor, but shall not be read to be an axis of symmetry unless expressly stated.

"Central axis" shall mean a longitudinal axis of a structure or portion thereof, but shall not be read to be an axis of symmetry unless expressly stated.

"Transverse dimension" of a component or feature shall mean a largest dimension of the component or feature measured perpendicularly to a central axis of the component or feature. For example, if a component is cylindrical, the transverse dimension is the diameter. If the component is a conical frustum, the transverse dimension is the largest diameter (e.g., the base) of the conical frustum.

"Frustum" shall mean a portion of a solid object residing between two parallel planes, the planes perpendicular to a central axis of the solid object (e.g., a conical frustum).

A "radial" from a central axis shall mean a line perpendicular to the central axis and extending outward from the central axis.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

Various example embodiments are directed to fixation devices in the form of bone anchors. More particularly, example embodiments are directed to bone anchors designed and constructed to interact with the bone at a plurality of non-overlapping annular locations spread around the bone anchor. More particularly still, example embodiments are directed to bone anchors that define a plurality of barbs that extend outward from an anchor central axis of the bone anchor, with each barb at unique annular or radial orientation relative to the anchor central axis. When inserted into a bone, each barb interacts with an inside diameter of a blind bore into the bone, each interaction at a unique radial orientation. In some example embodiments, the bone anchor defines a stack of frustums that are not coaxial, and each barb is defined by an outer portion of a frustum. In some cases, each frustum is a conical frustum.

FIG. 1 shows a perspective view of a bone anchor 100 in accordance with at least some embodiments. The example bone anchor 100 comprises a proximal head 102 on a proximal end 102 of the bone anchor 100. Disposed opposite the proximal head 102 is a distal tip 106 on a distal end 108 of the bone anchor 100. The bone anchor 100 defines a central axis 110, hereafter referred to as the "anchor central axis 110" to distinguish from other central axes discussed below. The proximal head 102 defines a central axis that is coaxial with the anchor central axis 110 (and thus the central axis of the proximal head 102 is not separately shown). The proximal head 102 defines a top surface 112. In example cases the top surface 112 defines a plane that is perpendicular to the anchor central axis 110. The proximal head 102 further defines an annular surface 114 that extends around the anchor central axis 110, and in example cases the annular surface 114 is perpendicular to the plane defined by the top surface 112. The example proximal head 102 further includes a shoulder region 116 defined between the annular surface 114 and the top surface 112, and in example cases the shoulder region 116 defines a rounded or smooth transition between the annular surface 114 and the top surface 112.

The proximal head 102 defines a transverse dimension. "Transverse dimension" shall mean a largest dimension measured perpendicularly to a central axis of the component or feature. In the case of the proximal head 102, and with the exception of the trough 118 (discussed more below), the proximal head 102 is right circular cylinder and thus the transverse dimension is the diameter of the right circular cylinder. Further as shown, the proximal head 102 defines a notch, valley, or trough 118. The trough 118 defines an open top and a closed bottom, and the channel created by the trough 118 runs parallel to the anchor central axis 110.

Figure 2:
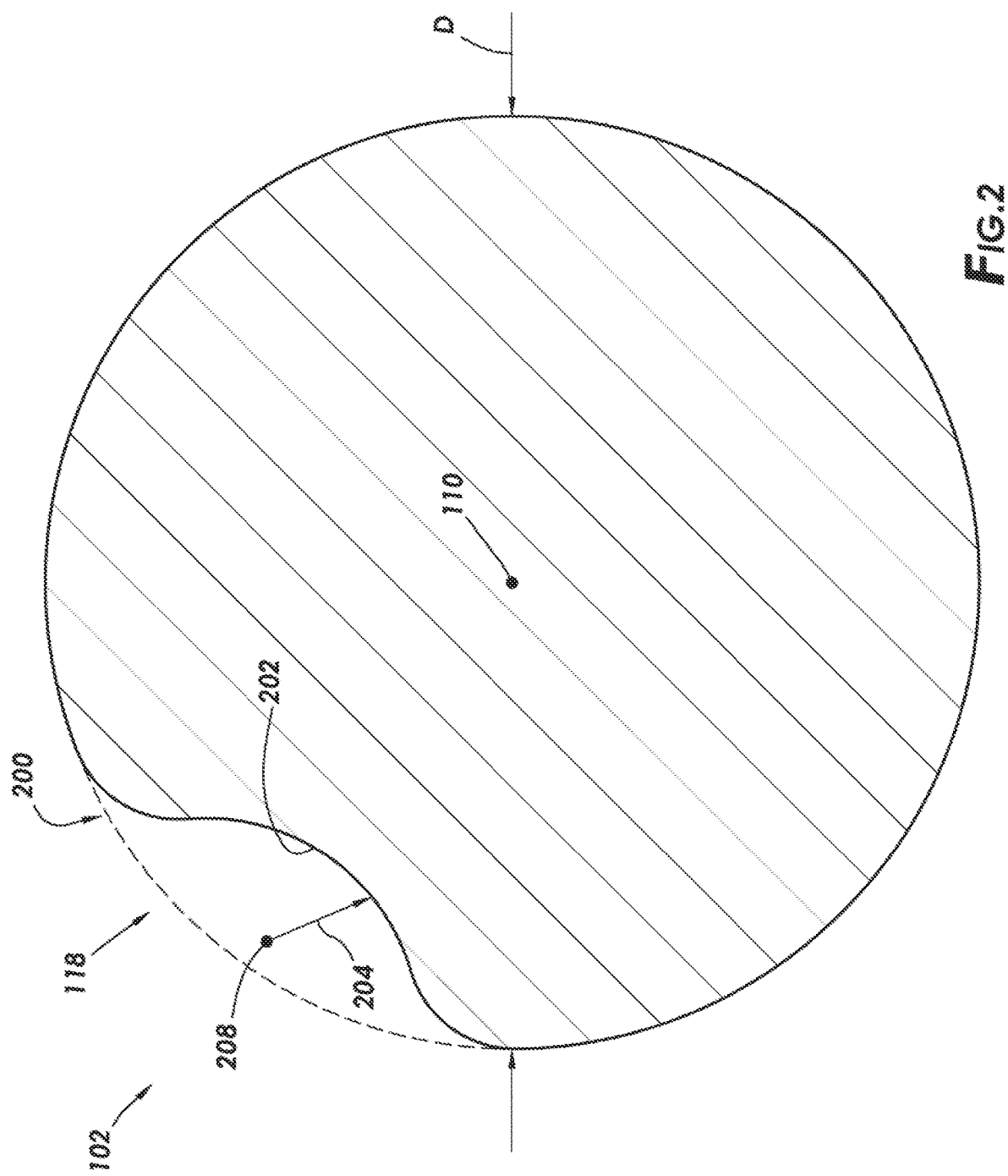
FIG. 2 shows a cross-sectional view of the proximal head taken substantially along line 2-2 of FIG. 1, and in accordance with at least some embodiments.

FIG. 2 shows a cross-sectional view of the proximal head 102 taken substantially along line 2-2 of FIG. 1, and in accordance with at least some embodiments. In particular, the proximal head 102 defines a central axis coaxial with the anchor central axis 110. The anchor central axis 110 is perpendicular to the plane of the page of FIG. 2, and thus is shown as a dot. With the exception of the trough 118, in the cross-sectional view of FIG. 2 the proximal head 102 has a circular cross-section (the portion over the trough 118 shown in dashed lines). It follows that the transverse dimension of the proximal head 102 is the diameter of the cross-section at a location other than the location of the trough 118. The trough 118 defines an open top 200 (along the dashed line), as well as a closed bottom 202. The closed bottom 202 of the trough 118 defines a radius of curvature (e.g., radius 204). The radii of curvature (including the radius of curvature 204) along a length of the proximal head 102 (the length measured parallel to the anchor central axis 110) may be equal. The origins of the radii of curvature taken together define a line 208 (in the view of FIG. 2, the line is perpendicular to the plane of the page and thus shown as a dot), and the line 208 is parallel to the anchor central axis 110. The trough 118 defines a channel through which a suture (not specifically shown) may run to reduce the chances of the suture contacting bone when the bone anchor is inserted into the bone. The trough 118 is not and shall not be considered a hole or aperture through the proximal head 102, and thus the example bone anchor 100 may be considered "eyeless" in comparison to related-art bone anchors.

Returning to FIG. 1, the example bone anchor 100 further defines a suture connection region or bollard 120. The bollard 120 is coupled to the proximal head 102. The bollard 120 has axial length (measured parallel to the anchor central axis 110), and the bollard 120 has a transverse dimension smaller than the transverse dimension of the proximal head 102. In the example case of FIG. 1, the bollard 120 comprises a right circular cylinder that defines a central axis that is coaxial with the anchor central axis 110, and the diameter of the right circular cylinder defines the transverse dimension of the bollard 120. The bollard 120 abuts the proximal head 102, and given the differences in transverse dimension between the bollard 120 and the proximal head 102, a shoulder 122 is defined between the bollard 120 and the proximal head 102. In use, a suture may be tied to the bollard 120, with the suture then running along the trough 118.

The distal tip 106 of the bone anchor 100 has a central axis that is coaxial with the anchor central axis 110 (and thus the central axis of the distal tip 106 is not separately shown). The distal tip 106 resides on the opposite end of the bone anchor 100 from the proximal head 102. In the example case of FIG. 1, the distal tip 106 defines a cone with an apex 124 and a base 126. It follows that a cross-section of the cone taken along the anchor central axis 110 would be triangular. The apex 124 of the cone defines a tip of the bone anchor 100, and the base is coupled to regions (discussed more below) that define the barbs. The distal tip 106 is designed and constructed to telescope into a blind bore into a bone to help guide or lead the bone anchor into position. In other example cases, the distal tip 106 may take any suitable shape sufficient to initially guide or lead the bone anchor 100 into position, such as a flat spade shape (which may also have a triangular cross-sectional shape in certain orientations). In some example cases, the transverse dimension of the distal tip 106 is smaller than the transverse dimension of the proximal head 102 and larger than the transverse dimension of the bollard 120.

Still referring to FIG. 1, the example bone anchor 100 comprises a plurality of frustums disposed between the distal tip 106 and the bollard 120. In particular, the example bone anchor 100 defines six frustums 128, 130, 132, 134, 136, and 138 disposed between the distal tip 106 and the bollard 120, though greater or fewer frustums may be present (e.g., between and including two and ten frustums, or between and including three and seven frustums). Each frustum of the example bone anchor 100 is a conical frustum, but other frustums may be used (e.g., frustums created between two parallel planes cut through a sphere, or frustums created by two parallel planes cut through a tear drop shape). Moreover, the frustums need not have the same shape.

Frustum 128 defines a central axis (not shown in FIG. 1), and the central axis is offset from and parallel to the anchor central axis 110. Stated otherwise, the central axis of the frustum 128 is not coaxial with the anchor central axis 110, the frustum 128 is shifted relative to the distal tip 106, and thus the frustum 128 is not fully aligned with the distal tip 106. In the view of FIG. 1, the frustum 128 is shifted downward relative to the distal tip 106. The relationship of the frustum 128 to the anchor central axis 110 shifts a portion of the base of the frustum outward to create a barb that helps hold the bone anchor 100 within the bone. The example frustum 128 has a narrow diameter portion and a wide diameter portion. The narrow diameter portion abuts the distal tip 106, and the wide diameter portion (which also defines the transverse dimension of the frustum 128) is closer to the proximal head 102. In some example cases the transverse dimension of the frustum 128 is the larger than the transverse dimension of the distal tip 106.

Frustum 130 defines a central axis (not shown in FIG. 1), and the central axis is offset from and parallel to the anchor central axis 110. Moreover, the central axis of the frustum 130 is offset from and parallel to the central axis of frustum 128. Stated otherwise, the central axis of the frustum 130 is not coaxial with the anchor central axis 110, and is not coaxial with the central axis of the frustum 128. The relationship of the frustum 130 to the anchor central axis 110 shifts a portion of the base of the frustum 130 outward to create a barb that helps hold the bone anchor 100 within the bone. The example frustum 130 has a narrow diameter portion and a wide diameter portion. The narrow diameter portion abuts the frustum 128, and the wide diameter portion (which also defines the transverse dimension of the frustum 130) is closer to the proximal head 102. In some example cases the transverse dimension of the frustum 130 is the same as the transverse dimension of the frustum 128.

Example frustums 132, 134, and 136 each have a central axis that is offset from and parallel to the anchor central axis 110. The central axis of each of the frustums 132, 134, and 136 is offset from and parallel to the central axis of the remaining frustums, with the offsets of each frustum in a different and unique radial direction. The relationship of the frustums to the anchor central axis 110 shifts a portion of the base of each frustum outward to create a barb that helps hold the bone anchor 100 within the bone. Each example frustum 132, 134, and 136 has a narrow diameter portion and a wide diameter portion. The narrow diameter portion abuts a contiguous distal frustum, and the wide diameter portion abuts a contiguous proximal frustum. In some example cases the transverse dimension of each frustum 132, 134, and 136 is the same, and the transverse dimension of the frustums 132, 134, and 136 are the same as the transverse dimension of the frustum 128.

Frustum 138 defines a central axis (not shown in FIG. 1), and in example cases the central axis of the frustum 138 is coaxial with the anchor central axis 110. The example frustum 138 has a narrow diameter portion and a wide diameter portion. The narrow diameter portion abuts the frustum 136, and the wide diameter portion (which also defines the transverse dimension of the frustum 138) abuts the bollard 120. In some example cases the transverse dimension of the frustum 138 is greater than the transverse dimension of the bollard 120, and thus the frustum 138 and the bollard 120 define a shoulder 140. The shoulder 140 and the shoulder 122 (between the bollard 120 and the proximal head 102) define a region to which a suture may be tied. In other example cases, the central axis of the frustum 138 may likewise be offset from and parallel to the anchor central axis 110 such that the frustum 138 also defines a barb. In example cases the transverse dimension of frustum 138 is the same as the transverse dimension of the other frustums 128, 130, 132, 134, and 136. In some example cases, the transverse dimension of the frustums are the same as the transverse dimension of the proximal head 102.

Figure 3:
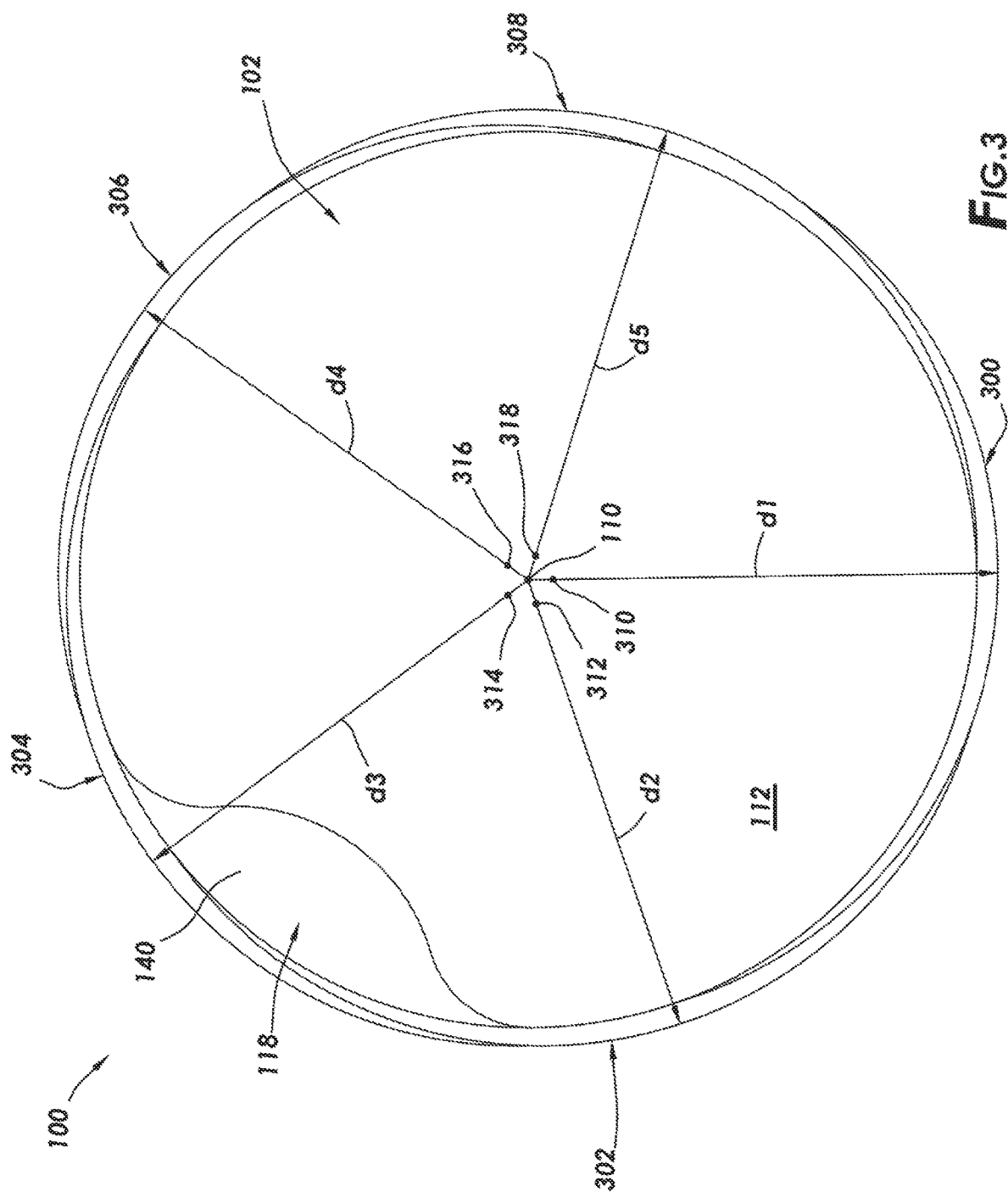
FIG. 3 shows an end elevation view of the bone anchor in accordance with at least some embodiments.

FIG. 3 shows an end elevation view of the bone anchor 100 in accordance with at least some embodiments. In particular, visible in FIG. 3 is the top surface 112 of the proximal head 102, along with the trough 118. Visible through the trough 118 is the shoulder 140. The anchor central axis 110 is perpendicular to the plane of the page, and thus the anchor central axis 110 is shown as point. Also visible in FIG. 3 are the barbs created by offsetting the central axes of the frustums away from the anchor central axis 110. In particular, visible in FIG. 3 are five barbs 300, 302, 304, 306, and 308.

Barb 300 in the example case of FIG. 3 corresponds to the frustum 136 (FIG. 1). In particular, the example frustum 136 has a central axis 310 offset from and parallel to the anchor central axis 110. In the view of FIG. 3, the central axis 310 of the frustum 136 is perpendicular to the plane of the page, and thus the central axis 310 of the frustum 136 is shown as point. The barb 300 may thus correspond to the portion of the frustum 136 that extends beyond the transverse dimension of the proximal head 102 (and the bollard 120 (FIG. 1)). It follows that the distance the barb 300 extends radially outward beyond the proximal head 102 is equal the distance between the central axis 310 and the anchor central axis 110 (the distance measured perpendicularly to each axis). The barb 300 created by the frustum 136 is thus coupled to the bollard (by way of frustum 138 (FIG. 1)). The barb 300 extends outward a distance d1 measured perpendicularly from the anchor central axis 110, the distance d1 is greater than half the transverse dimension of the bollard 120 (FIG. 1), and in some cases the distance d1 is greater than half the transverse dimension the proximal head 102.

Barb 302 in the example case of FIG. 3 corresponds to the frustum 134 (FIG. 1). In particular, the example frustum 134 has a central axis 312 offset from and parallel to the anchor central axis 110. In the view of FIG. 3, the central axis 312 of the frustum 134 is perpendicular to the plane of the page, and thus the central axis 312 of the frustum 134 is shown as point. The barb 302 may thus correspond to the portion of the frustum 134 that extends beyond the transverse dimension of the proximal head 102 (and the bollard 120 (FIG. 1)). It follows that the distance the barb 302 extends radially outward beyond the proximal head 102 is equal the distance between the central axis 312 and the anchor central axis 110 (the distance measured perpendicularly to each axis). The barb 302 extends outward a distance d2 measured perpendicularly from the anchor central axis 110, the distance d2 is greater than half the transverse dimension of the bollard 120 (FIG. 1), and in some cases the distance d2 is greater than half the transverse dimension the proximal head 102.

Barb 304 in the example case of FIG. 3 corresponds to the frustum 132 (FIG. 1). In particular, the example frustum 132 has a central axis 314 offset from and parallel to the anchor central axis 110. In the view of FIG. 3, the central axis 314 of the frustum 132 is perpendicular to the plane of the page, and thus the central axis 314 of the frustum 132 is shown as point. The barb 304 may thus correspond to the portion of the frustum 132 that extends beyond the transverse dimension of the proximal head 102 (and the bollard 120 (FIG. 1)). It follows that the distance the barb 304 extends radially outward beyond the proximal head 102 is equal the distance between the central axis 314 and the anchor central axis 110 (the distance measured perpendicularly to each axis). The barb 304 extends outward a distance d3 measured perpendicularly from the anchor central axis 110, the distance d3 is greater than half the transverse dimension of the bollard 120 (FIG. 1), and in some cases the distance d3 is greater than half the transverse dimension the proximal head 102.

Barb 306 in the example case of FIG. 3 corresponds to the frustum 130 (FIG. 1). In particular, the example frustum 130 has a central axis 316 offset from and parallel to the anchor central axis 110. In the view of FIG. 3, the central axis 316 of the frustum 130 is perpendicular to the plane of the page, and thus the central axis 316 of the frustum 130 is shown as point. The barb 306 may thus correspond to the portion of the frustum 130 that extends beyond the transverse dimension of the proximal head 102 (and the bollard 120 (FIG. 1)). It follows that the distance the barb 306 extends radially outward beyond the proximal head 102 is equal the distance between the central axis 316 and the anchor central axis 110 (the distance measured perpendicularly to each axis). The barb 306 extends outward a distance d4 measured perpendicularly from the anchor central axis 110, the distance d4 is greater than half the transverse dimension of the bollard 120 (FIG. 1), and in some cases the distance d4 is greater than half the transverse dimension the proximal head 102.

Barb 308 in the example case of FIG. 3 corresponds to the frustum 128 (FIG. 1). In particular, the example frustum 128 has a central axis 318 offset from and parallel to the anchor central axis 110. In the view of FIG. 3, the central axis 318 of the frustum 128 is perpendicular to the plane of the page, and thus the central axis 318 of the frustum 128 is shown as point. The barb 308 may thus correspond to the portion of the frustum 128 that extends beyond the transverse dimension of the proximal head 102 (and the bollard 120 (FIG. 1)). It follows that the distance the barb 308 extends radially outward beyond the proximal head 102 is equal the distance between the central axis 318 and the anchor central axis 110 (the distance measured perpendicularly to each axis). The barb 308 extends outward a distance d5 measured perpendicularly from the anchor central axis 110, the distance d5 is greater than half the transverse dimension of the bollard 120 (FIG. 1), and in some cases the distance d5 is greater than half the transverse dimension the proximal head 102.

In the example case of FIG. 3, the distance that each barb extends outward relative to the anchor central axis 110 is the same; however, the distance that each barb ends outward need not be the same. For example, barbs closer to the distal end 108 (FIG. 1) of the bone anchor 100 may extend a greater distance owing to the fact there is more bone between the barb and the surface of the bone. Similarly, barbs closer to the proximal end 104 (FIG. 1) of the bone anchor 100 may extend a lesser distance (relative to the barbs at the distal end 108) owing to the fact there is less bone between the barb and the surface of the bone, which may reduce the chance of bone breakage (e.g., flaking). And again, while five barbs are shown in FIG. 3, greater or fewer barbs (and thus greater or fewer frustums) may be implemented. The discussion now turns to radial orientation of each barb in accordance with example embodiments.

Figure 4:
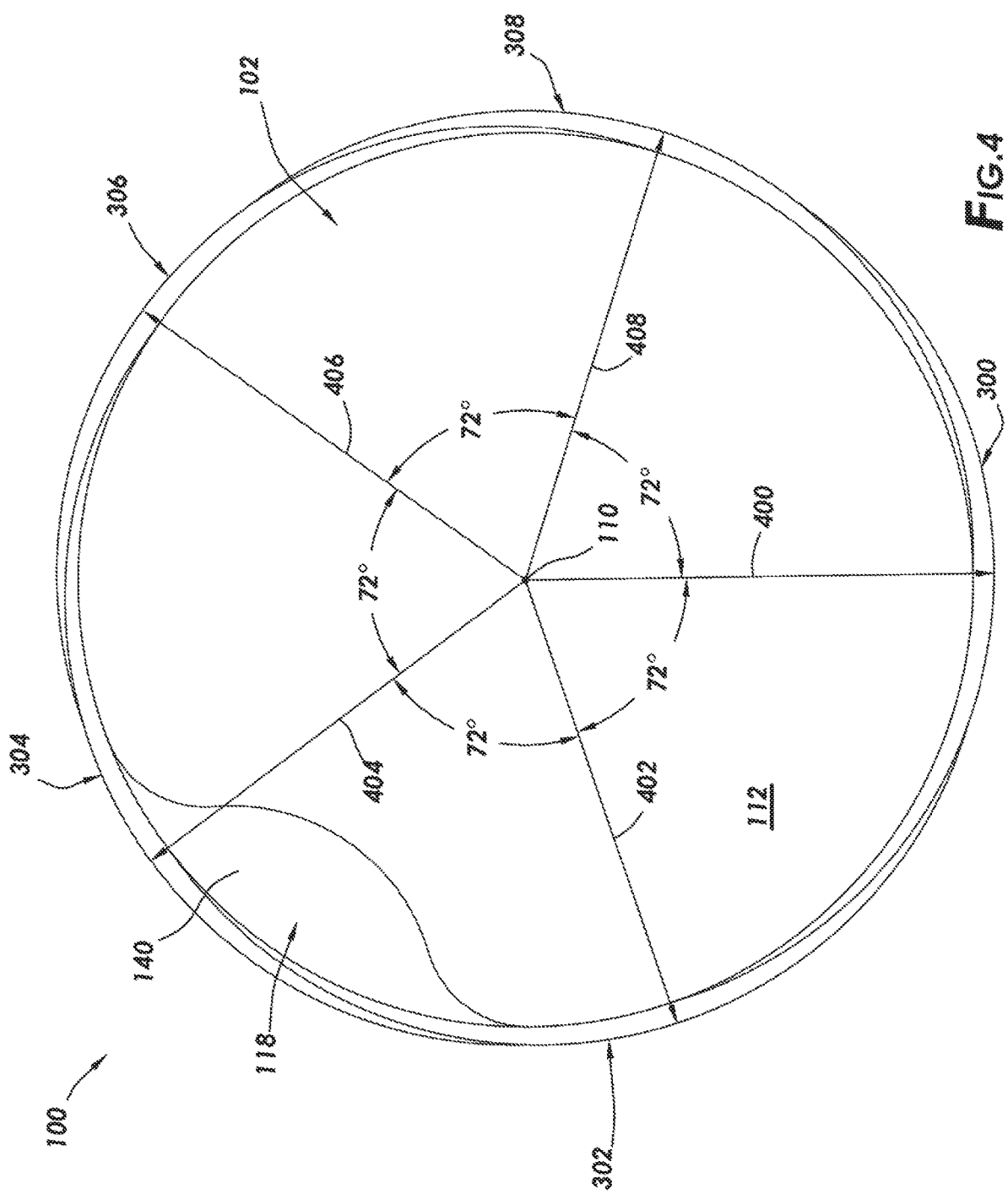
FIG. 4 shows an end elevation view of the bone anchor 100 in accordance with at least some embodiments.

FIG. 4 shows an end elevation view of the bone anchor 100 in accordance with at least some embodiments. In particular, visible in FIG. 4 is the top surface 112 of the proximal head 102, along with the trough 118. Visible through the trough 118 is the shoulder 140. The anchor central axis 110 is perpendicular to the plane of the page, and thus the anchor central axis 110 is shown as a point. Also visible in FIG. 4 are the barbs created by offsetting the central axes of the frustums away from the anchor central axis 110. In particular, visible in FIG. 4 are the five example barbs 300, 302, 304, 306, and 308. In accordance with example embodiments, each barb extends outward at an annular location or a radial orientation from the anchor central axis different and distinct from the radial orientation of the other barbs. For example, the barb 300 extends outward at a radial 400, the radial 400 extending from the anchor central axis 110. The barb 302 extends outward at a radial 402, the radial 402 extending from the anchor central axis 110. The barb 304 extends outward at a radial 404, the radial 404 extending from the anchor central axis 110. The barb 306 extends outward at a radial 406, the radial 406 extending from the anchor central axis 110. The barb 308 extends outward at a radial 408, the radial 408 extending from the anchor central axis 110. Thus, the radial orientation of each barb differs by an angular measure. In the example case of five barbs evenly spaced around the bone anchor 100, the radial orientation of each radial differs by 72 angular degrees. If more barbs are present, the radial orientation may differ by a lesser amount (e.g., 36 angular degrees for a bone anchor with ten barbs). Oppositely, if fewer barbs are present the radial orientation may differ by a greater amount (e.g., 120 angular degrees for a bone anchor with three barbs).

In some example cases the locations of the barbs are "stair stepped" around the bone anchor sequentially. For example, and referring simultaneously to FIGS. 1 and 4, the first barb 300 (created by the frustum 136 closer to the bollard 120) may define a first radial orientation. The barb 302 (created by the frustum 134) may be the next contiguous barb and have a radial orientation 72 angular degrees from the first barb 300. The barb 304 (created by the frustum 132) may be the next contiguous barb and have a radial orientation 72 angular degrees from the barb 302. The barb 306 (created by the frustum 130) may be the next contiguous barb and have a radial orientation 72 angular degrees from the barb 304. The barb 308 (created by the frustum 128) may be the next contiguous barb and have a radial orientation 72 angular degrees from the barb 306. Thus, the barb locations may spiral around the bone anchor 100. However, in other example cases the barbs need not spiral around the bone anchor 100. It follows the radial orientations of the barbs may be designed and constructed such that contiguous barbs differ in radial orientation by more than the total number of barbs divided by 360 angular degrees. For example, considering the five example barbs and further considering barb 300 as the starting point, the next contiguous barb (e.g., the barb 304) may be 144 angular degrees from barb 300. From barb 304 the next contiguous barb (e.g., the barb 308) may be 144 angular degrees from barb 304. From barb 308 the next contiguous barb (e.g., the barb 302) may be 144 angular degrees from barb 308. From barb 302 the next contiguous barb (e.g., the barb 306) may be 144 angular degrees from barb 302.

Figure 5:
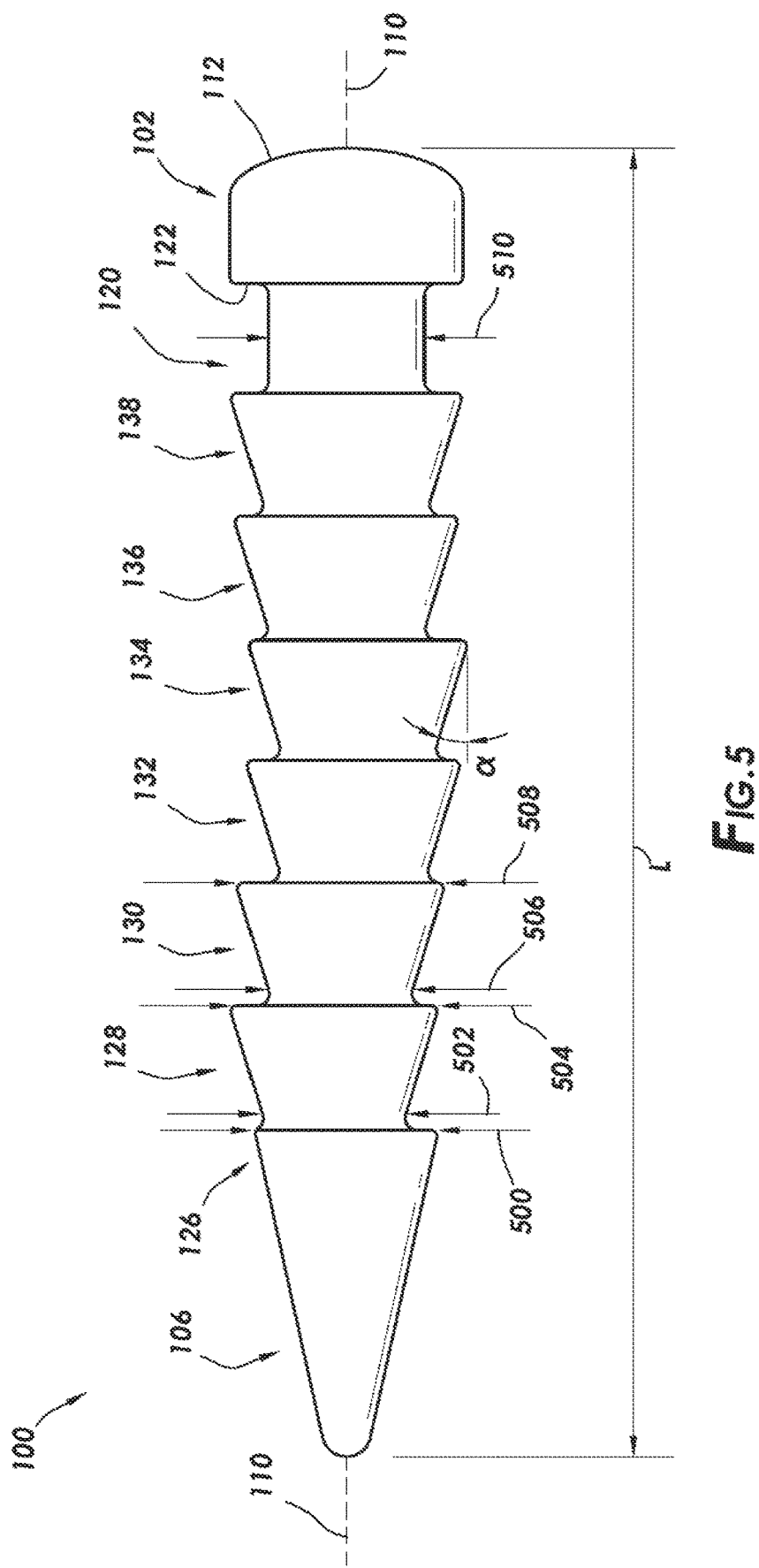
FIG. 5 shows a side-elevation view of a bone anchor in accordance with at least some embodiments.

FIG. 5 shows a side-elevation view of a bone anchor in accordance with at least some embodiments. In particular, FIG. 5 shows the example bone anchor 100 comprising: the distal tip 106; five example frustums 128, 130, 132, 134, 136 and 138; the bollard 120; the proximal head 102; and the anchor central axis 110. FIG. 5 also shows various example dimensions of the bone anchor 100. In particular, the distal tip 106 defines a base diameter 500 at its base 126 (e.g., the transverse dimension). In example cases, the base diameter 500 is based on the diameter of a pilot hole or blind bore into the bone and into which the bone anchor 100 will be inserted. In example cases the base diameter 500 is selected to be about the same as the diameter of the blind bore. For example, if the blind bore has a diameter of 2.0 millimeters (mm), the base diameter 500 will be about 2.0 mm.

The frustum 128 is contiguous with the distal tip 106. The frustum 128 defines a first diameter at its apex that abuts the distal tip 106, and a second diameter at its base that defines the transverse dimension of the frustum 128. By its nature, the apex diameter 502 of frustum 128 is smaller than the base diameter 504. The apex diameter 502 is selected based on the diameter of the blind bore into which the bone anchor 100 will be inserted. In example cases the apex diameter 502 is selected to be about the same as the diameter of the blind bore. For example, if the blind bore has a diameter of 2.0 mm, the apex diameter 502 will be about 2.0 mm. Likewise, the base diameter 504 is selected based on the diameter of the blind bore into which the bone anchor 100 will be inserted. In example cases the base diameter 504 is selected to be between and including 0.25 to 1.0 mm larger than the diameter of the blind bore. For example, if the blind bore has a diameter of 2.0 millimeters, the base diameter 504 may be about 2.5 mm.

The frustum 130 is contiguous with the frustum 128. The frustum 130 defines a first diameter at its apex that abuts the frustum 128, and a second diameter at its base that defines the transverse dimension of the frustum 130. By its nature, the apex diameter 506 of the frustum 130 is smaller than the base diameter 508. The apex diameter 506 is selected based on the diameter of the blind bore into which the bone anchor 100 will be inserted. In example cases the apex diameter 506 is selected to be about the same as the diameter of the blind bore. For example, if the pilot hole has a diameter of 2.0 mm, the apex diameter 506 will be about 2.0 mm. Likewise, the base diameter 508 is selected based on the diameter of the blind bore into which the bone anchor 100 will be inserted. In example cases the base diameter 506 is selected to be between and including 0.25 to 1.0 mm larger than the diameter of the blind bore. For example, if the pilot hole has a diameter of 2.0 millimeters, the base diameter 506 may be about 2.5 mm. The description with regard to the frustum 130 is equally applicable to the frustums 132, 134, 136, and 138, and thus the description with respect to each of the remaining frustums will not be repeated so as not to unduly lengthen the specification.

The annular surface of the distal tip 106, as well as the annular surface of each frustum 128, 130, 132, 134, 136, and 138, define a slope or angle between a line parallel to the anchor central axis and the annular surface. Referring to the frustum 134 as representative, the angle α between the annular surface a line parallel to the anchor central axis 110 may take any suitable angle. For example, the angle α may be between and including 10 and 20 angular degrees, and in some cases between and including 12 and 15 angular degrees. In some cases, the angle α may the same for the distal tip 106 as well all the frustums, but in other cases the angle α for the distal tip 106 may be larger or smaller. In some cases, the angle α is the same for all the frustums 128, 130, 132, 134, 136, and 138.

Still moving to the right in FIG. 5, the example bollard 120 couples between the frustum 138 and the proximal head 102. The example bollard 120 defines a right circular cylinder, and thus the transverse dimension of the bollard 120 is its diameter 510. The diameter 510 of the bollard 120 is selected based on the diameter of the blind bore into which the bone anchor 100 will be inserted, and in particular the diameter 510 of the bollard 120 is selected to be between and including 0.25 to 1.0 mm smaller than the diameter of the blind bore. For example, if the blind bore has a diameter of 2.0 mm, the diameter 510 of the bollard 120 may be about 2.5 mm. It follows that in example cases the transverse dimension of the bollard 120 is smaller than the apex diameters of the frustums. Stated differently, the transverse dimensions of the frustums may be greater than the transverse dimension of the bollard 120.

The example bone anchor 100 defines a length L measured between the distal end 108 of the distal tip 106 and the top surface 112 of the proximal head 102. In an example case in which the transverse dimension of the proximal head 102 is 2.5 mm, the bone anchor may have a length of about 13.6 mm, but longer and shorter bone anchors may be used (e.g., between and including 10 mm to 15 mm). An example bone anchor 100 having a proximal head 102 with a transverse dimension of 2.5 mm, a length of about 13 mm, and inserted into a blind bore into a bone analog (the blind bore having a diameter of 2.0 mm) had a pullout strength of about 40-50 pounds (measured parallel to the anchor central axis).

One, non-limiting, theory of why the example bone anchor 100 has a relatively high pullout strength is based on the non-overlapping locations of the barbs formed by the frustums. In particular, related-art bone anchors have a plurality of ribs (defined by a plurality of annular grooves), with each rib having the same diameter. During installation, the bone anchors are pushed into a blind bore into the bone. Once the second or third rib is pushed past a particular location within the blind bore into the bone, the bone anchor effectively widens the diameter of the blind bore. The ribs at the proximal end of the bone anchor may provide little or no pullout holding strength. Stated otherwise, only the first few ribs at the distal tip of the related-art bone anchors may substantially contribute to the holding strength of the bone anchors.

Referring again to FIG. 3, in accordance with example embodiments each example barb 300, 302, 304, 306, and 308 has a portion that extends outward at a unique annular location around the bone anchor and/or a unique radial orientation relative to the anchor central axis 110. In example embodiments no other barb of the bone anchor extends outward in exactly the same radial orientation. Thus, using the example bone anchor 100 each barb singly and uniquely contacts the bone at the radial orientation of the barb. It follows that each and every barb substantially contributes to the pullout strength of the example bone anchor 100, thus increasing the pullout strength.

Figure 6:
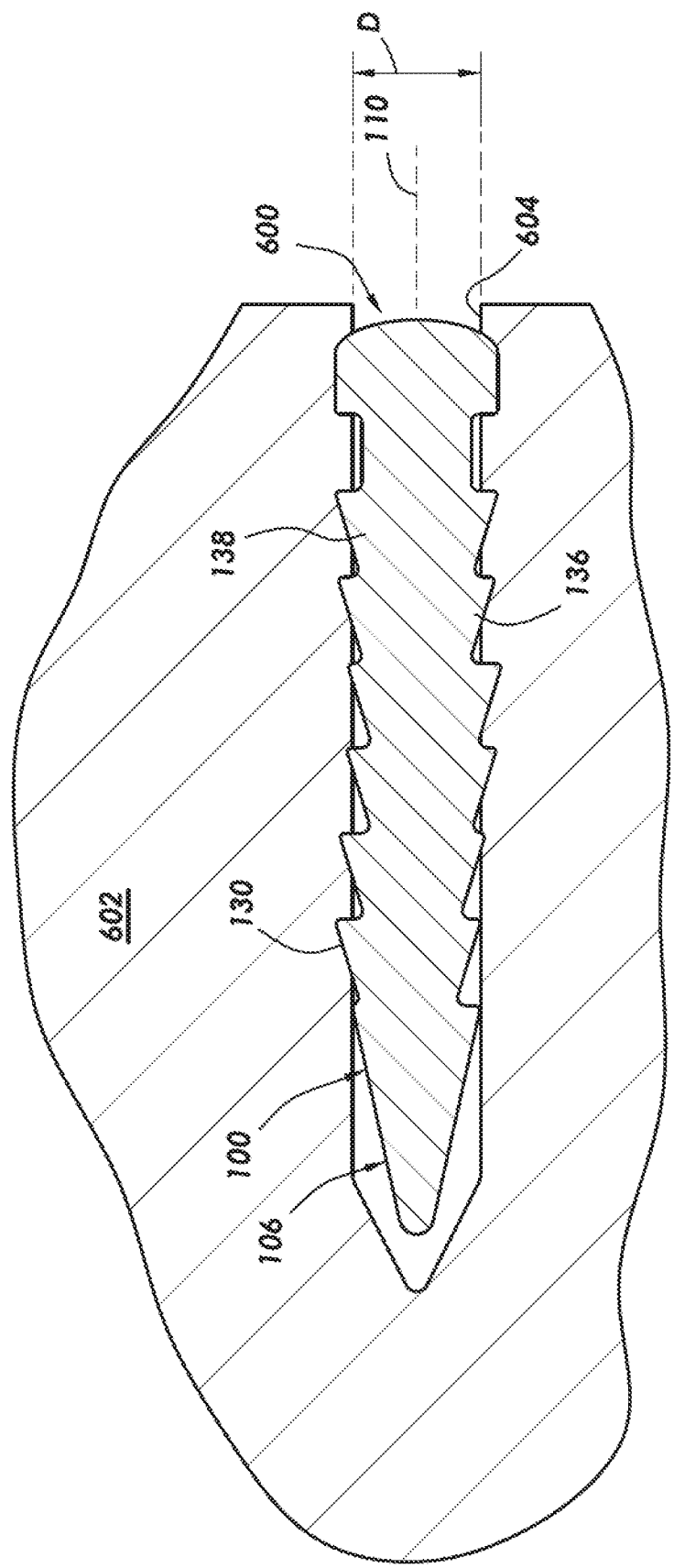
FIG. 6 shows a cross-sectional view of a bone anchor in bone, in accordance with at least some embodiments.

FIG. 6 shows a cross-sectional view of a bone anchor in a bone, in accordance with at least some embodiments. In particular, visible in FIG. 6 is the example bone anchor 100 disposed within a blind bore 600 within a section of a bone 602 (e.g., the greater tuberosity of the humeral head). The blind bore 600 defines a diameter D (e.g., 2.0 mm). The bone anchor 100 is telescoped with within the blind bore 600. In example embodiments, the transverse dimension of the distal tip 106 is about the same as the diameter of the blind bore 600 (e.g., 2.0 mm). Further in example embodiments, each frustum has a transverse dimension slightly larger than the diameter of the blind bore 600, and thus each frustum contacts the inside diameter 604 of the blind bore 600, and may in fact (and as shown) extend into the bone 602. Moreover, because of the offsetting central axis of each frustum, each frustum predominantly contacts the inside diameter 604 of the blind bore 600 at a unique annular location around the bone anchor and/or a unique radial orientation relative to the anchor central axis 110. In the view of FIG. 6, frustum 130 contacts the inside diameter 604 and extends into the bone predominantly on the upper side of the blind bore 600, and frustum 136 contacts the inside diameter 604 and extends into the bone predominantly on the lower side of the blind bore 600. The remaining frustums likewise contact the inside diameter 604 and extend into the bone 602 at their respective unique locations, but such is not visible in the cross-sectional view of the FIG. 6.

In example embodiments the proximal head 102 likewise has a transverse dimension slightly larger than the diameter of the blind bore 600, and may thus also extend slightly into the bone. Because the central axis of the proximal head 102 is coaxial with the anchor central axis 110, the distance the proximal head 102 may extend into the bone is less than a maximum distance any of the frustums (with an offset central axis) extend into the bone. Finally, in the example embodiment the central axis of the frustum 138 is coaxial with the anchor central axis 110, and thus the transverse dimension of the frustum 138 may extend into the bone a similar distance as the proximal head 102.

In example cases, the bone anchor 100 may be made of a thermoplastic, such as polyether ether ketone (PEEK), such as medical PEEK available from Imbivio Ltd (www.imbivio.com). Other suitable components may be selected, including in certain situations metallic materials (e.g., titanium). In some cases the example bone anchor 100 may be milled from a billet of material, such as on a small lathe. In other cases, the example bone anchor 100 may be molded (e.g., injection molded).

In example embodiments the barbs are created by frustums whose central axes are offset from and parallel to the anchor central axis 110. Thus, the barbs in the example cases are regions of a circular cross-section that extends beyond the transverse dimension of: the distal tip 106; the bollard 120; and/or the proximal head 102. Looking along the anchor central axis 110 (e.g., from the proximal end), the portion of each circular cross-section that extends outward takes the shape of a crescent. Depending on the number of frustums and thus the number of crescents, there may be annular overlap at the edges of the crescents. For example, in the view of FIG. 3 the crescent that forms barb 300 is fully visible, but one edge of each of the crescents forming barbs 302, 304, and 306, are partially obscured. Both edges of the crescent forming barb 308 are obscured. Nevertheless, each crescent has at least a portion of its annular span that extends in the radial orientation.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. An apparatus comprising:
    a bone anchor including
        a proximal head that defines a central axis and a transverse dimension, the central axis coaxial with an anchor central axis;
        a bollard having transverse dimension smaller than the transverse dimension of the proximal head, and the bollard coupled to the proximal head;
        a plurality of barbs;
        the plurality of barbs each defined by a separate frustum spaced axially from one another along the anchor central axis, said plurality of barbs including a first barb defined by a first frustum in spaced relation along the anchor central axis from the bollard, the first barb extends outward at a first unique maximum radial from the anchor central axis a first distance measured perpendicularly from the anchor central axis, the first distance greater than half the transverse dimension of the bollard;
        the plurality of barbs including a second barb defined by a second frustum in spaced relation along the anchor central axis from both the bollard and the first barb, the second barb extends outward at a second unique maximum radial from the anchor central axis a second distance measured perpendicularly from the anchor central axis, the second distance greater than half the transverse dimension of the bollard; and
        wherein each of the plurality of barbs is spaced axially from the other barbs along the anchor central axis and each barb extends outward along circumferentially offset radials from one another.

2. The bone anchor of claim 1 wherein the first distance and the second distance are equal to half the transverse dimension of the proximal head.

3. The bone anchor of claim 1 further comprising a distal tip having a central axis coaxial with the anchor central axis, the distal tip coupled to the first and second barbs on an opposite end from the proximal head.

4. The bone anchor of claim 3 the wherein the distal tip has a cross-sectional shape taken along the anchor central axis that is triangular.

5. An apparatus comprising:
    a bone anchor including
        a proximal head that defines a central axis and a transverse dimension, the central axis coaxial with an anchor central axis;
        a bollard having transverse dimension smaller than the transverse dimension of the proximal head, and the bollard coupled to the proximal head;
        a plurality of barbs;
        the plurality of barbs each defined by a separate frustum spaced axially from one another along the anchor central axis, said plurality of barbs including a first barb defined by a first frustum in spaced relation along the anchor central axis from the bollard, the first barb extends outward a first radial from the anchor central axis a first distance measured perpendicularly from the anchor central axis, the first distance greater than half the transverse dimension of the bollard;
        the plurality of barbs including a second barb defined by a second frustum in spaced relation along the anchor central axis from both the bollard and the first barb, the second barb extends outward at a second radial from the anchor central axis a second distance measured perpendicularly from the anchor central axis, the second distance greater than half the transverse dimension of the bollard;
        wherein each of the plurality of barbs is spaced axially from the other barbs along the anchor central axis and each barb extends outward along circumferentially offset radials from one another; and wherein the distal tip is conical first frustum defines a first central axis and a transverse dimension, the first central axis being parallel to the anchor central axis, the transverse dimension of the first frustum being less than twice the first distance, and wherein the second frustum defines a second central axis and a transverse dimension, the second central axis being parallel to both the anchor central axis and the first central axis, the transverse dimension of the second frustum being less than twice the second distance.

6. The bone anchor of claim 3 wherein the transverse dimension of the distal tip is smaller than the transverse dimension of the proximal head and larger than the transverse dimension of the bollard.

7. The bone anchor of claim 1 wherein the proximal head further comprises a trough with an open top and a closed bottom, the trough runs parallel to the anchor central axis.

8. The bone anchor of claim 1 wherein the plurality of barbs include a third barb defined by a third frustum in spaced relation along the anchor central axis from both the bollard and the first and second barbs, the third barb extends outward a third distance measured perpendicularly from the anchor central axis, the third distance greater than half the transverse dimension of the bollard, and the third barb extends outward at a third unique maximum radial from the anchor central axis parallel to the anchor central axis.

9. The bone anchor of claim 1:
    wherein the bollard further comprises a cylindrical section that defines a central axis that is coaxial with the anchor central axis, a diameter of the cylindrical section defines the transverse dimension of the bollard; and
    a shoulder defined at an intersection of the bollard and the proximal head.

10. An apparatus comprising:
    a bone anchor including
        a proximal head that defines a central axis and a transverse dimension, the central axis coaxial with an anchor central axis;
        a bollard having transverse dimension smaller than the transverse dimension of the proximal head, and the bollard coupled to the proximal head;
        a first barb coupled to the bollard, the first barb extends outward a first distance measured perpendicularly from the anchor central axis, the first distance greater than half the transverse dimension of the bollard, and the first barb extends outward at a first radial from the anchor central axis;
        a second barb contiguous with the first barb, the second barb extends outward a second distance measured perpendicularly from the anchor central axis, the second distance greater than half the transverse dimension of the bollard, and the second barb extends outward at a second radial from the anchor central axis, the second radial at a second rotational orientation at least 36 angular degrees from the first radial;

a first frustum that defines first central axis and a transverse dimension, the first central axis parallel to the anchor central axis, the transverse dimension of the first frustum being less than twice the first distance, and wherein a portion of the first frustum defines the first barb; and a second frustum that defines second central axis and a transverse dimension, the second central axis parallel to the anchor central axis and also parallel to the first central axis, the transverse dimension of the second frustum being less than twice the second distance, and wherein a portion of the second frustum defines the second barb.

11. The bone anchor of claim 10 further comprising:
wherein the first frustum is a first conical frustum; and
wherein the second frustum is a second conical frustum.

12. An apparatus comprising:
a bone anchor for use within a bone, the bone anchor including
 a distal tip that is conical and defines an anchor central axis;
 a first frustum coupled to the distal tip, the first frustum defines first central axis and a transverse dimension, the first central axis parallel to the anchor central axis, and the first central axis offset along a first radial from the anchor central axis;
 a second frustum coupled to the first frustum opposite the distal tip, the second frustum defines second central axis and a transverse dimension, the second central axis parallel to the anchor central axis, and the second central axis offset along a second radial from the anchor central axis, the second radial at least 36 angular degrees from the first radial;
 a third frustum coupled to the second frustum opposite the first frustum, the third frustum defines third central axis and a transverse dimension, the third central axis parallel to the anchor central axis, the third central axis offset along a third radial from the anchor central axis, the third radial at least 36 angular degrees from the second radial;
 a bollard having a central axis and transverse dimension, and the bollard coupled to the third frustum opposite the second frustum, and the central axis of the bollard coaxial with the anchor central axis;
 a proximal head that defines a central axis, the proximal head contiguous with the bollard, and the central axis of the proximal head coaxial with the anchor central axis;
 the transverse dimensions of the first, second, and third frustums are larger than the transverse dimension of the bollard.

13. The anchor of claim 12 further comprising the distal tip defines a transverse dimension, and the transverse dimension of the distal tip is equal to or smaller than the transverse dimension of the first frustum.

14. The anchor of claim 12 further comprising the proximal head defines a transverse dimension that is larger than the transverse dimension of the bollard, and the transverse dimension of the proximal head is equal to or smaller than the transverse dimension of the third frustum.

15. The anchor of claim 12 wherein the proximal head further comprises a trough with an open top and a closed bottom, the trough runs parallel to the anchor central axis.

16. The anchor of claim 15 wherein the closed bottom of the trough defines radii of curvature that are equal, and the radii of curvature define a line parallel to the anchor central axis.

17. The anchor of claim 12 further comprising the first frustum, the second frustum, and the third frustum are all conical frustums.

18. The anchor of claim 12 wherein the first frustum defines a first crescent portion centered at the first radial, the first crescent portion defined between a radius of curvature centered at the first central axis and the radius of curvature centered at the anchor central axis.

19. The anchor of claim 18 wherein the second frustum defines a second crescent portion centered at the second radial, the second crescent portion defined between the radius of curvature centered at the second central axis and the radius of curvature centered at the anchor central axis.

20. The anchor of claim 19 wherein the third frustum defines a third crescent portion centered at the third radial, the third crescent portion defined between the radius of curvature centered at the third central axis and the radius of curvature centered at the anchor central axis.

* * * * *

UNITED STATES PATENT AND TRADEMARK OFFICE
CERTIFICATE OF CORRECTION

PATENT NO. : 11,844,509 B2
APPLICATION NO. : 16/846711
DATED : December 19, 2023
INVENTOR(S) : Donald A. Williams et al.

It is certified that error appears in the above-identified patent and that said Letters Patent is hereby corrected as shown below:

In the Claims

In Column 11, Line 50, "the wherein the" should be --wherein the--

In Column 12, Line 17, "distal tip is conical" should be --the first frustum--

Signed and Sealed this
Tenth Day of September, 2024

Katherine Kelly Vidal
*Director of the United States Patent and Trademark Office*